(12) United States Patent
Suzushima

(10) Patent No.: US 7,229,407 B2
(45) Date of Patent: Jun. 12, 2007

(54) CAPSULE ENDOSCOPE WITH ELECTROLUMINESCENCE LIGHT SOURCE

(75) Inventor: Hiroshi Suzushima, Nagano (JP)

(73) Assignee: Olympus Corporation, Tokyo (JP)

( * ) Notice: Subject to any disclaimer, the term of this patent is extended or adjusted under 35 U.S.C. 154(b) by 502 days.

(21) Appl. No.: 10/799,796

(22) Filed: Mar. 12, 2004

(65) Prior Publication Data

US 2005/0043586 A1    Feb. 24, 2005

(30) Foreign Application Priority Data

Mar. 17, 2003    (JP) .............................. 2003-072665

(51) Int. Cl.
*A61B 1/06*    (2006.01)
(52) U.S. Cl. ...................... 600/179; 600/178; 600/160; 362/574
(58) Field of Classification Search ................ 600/178, 600/179, 160, 476, 407; 362/572, 574
See application file for complete search history.

(56) References Cited

U.S. PATENT DOCUMENTS

| 3,417,745 | A | * | 12/1968 | Sheldon ...................... 600/167 |
| 3,775,631 | A | * | 11/1973 | Morikawa .................... 313/502 |
| 4,233,615 | A | * | 11/1980 | Takemoto et al. ........... 257/273 |
| 5,363,135 | A | * | 11/1994 | Inglese ......................... 348/70 |
| 6,920,165 | B2 | * | 7/2005 | Jewell et al. ............. 372/45.01 |
| 2002/0093743 | A1 | * | 7/2002 | Miyamae et al. ........... 359/619 |
| 2002/0103417 | A1 | * | 8/2002 | Gazdzinski ................. 600/109 |
| 2002/0185588 | A1 | * | 12/2002 | Wagner et al. ........... 250/214.1 |
| 2003/0072538 | A1 | * | 4/2003 | Jin et al. ....................... 385/89 |
| 2003/0130562 | A1 | * | 7/2003 | Barbato et al. ............. 600/109 |
| 2003/0167000 | A1 | * | 9/2003 | Mullick et al. ............. 600/424 |
| 2003/0189742 | A1 | * | 10/2003 | Kobayashi ................... 359/202 |
| 2003/0205707 | A1 | * | 11/2003 | Chi-Ming ..................... 257/40 |
| 2003/0234607 | A1 | * | 12/2003 | Kim et al. ................... 313/502 |
| 2004/0027459 | A1 | * | 2/2004 | Segawa et al. ........ 348/207.99 |
| 2004/0171914 | A1 | * | 9/2004 | Avni ........................... 600/160 |
| 2005/0151489 | A1 | * | 7/2005 | Lys et al. .................... 315/308 |
| 2006/0004256 | A1 | * | 1/2006 | Gilad et al. ................. 600/160 |
| 2006/0036131 | A1 | * | 2/2006 | Glukhovsky et al. ....... 600/160 |

FOREIGN PATENT DOCUMENTS

| JP | 8-117184 | 5/1996 |
| JP | 10-267634 | 10/1998 |
| JP | 11-253398 | 9/1999 |
| JP | 2001-091860 | 4/2001 |

\* cited by examiner

*Primary Examiner*—John P. Leubecker
(74) *Attorney, Agent, or Firm*—Scully, Scott, Murphy & Presser, P.C.

(57) ABSTRACT

A capsule endoscope includes a capsule portion. The capsule portion includes at least an observation optical unit having an image pick-up element and an optical lens that forms an objective optical system, an illuminating unit having an illuminating substrate, an electroluminescence light source, and a light-emitting control circuit, a peripheral-circuit part which forms various circuits having a signal processing circuit, a receiving and transmitting circuit, and a control circuit, and a power source unit which supplies power to the observation optical unit, the illuminating unit, and the peripheral-circuit part.

8 Claims, 5 Drawing Sheets

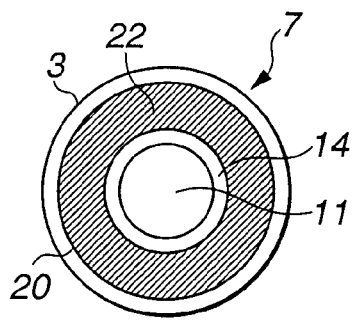
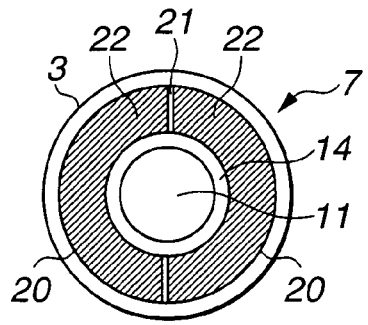
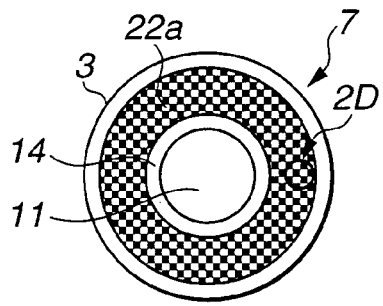
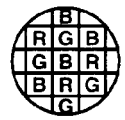
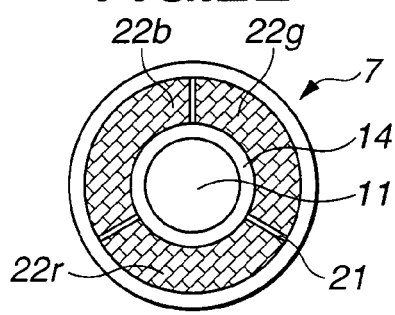
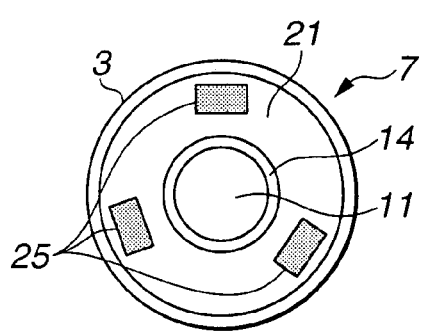
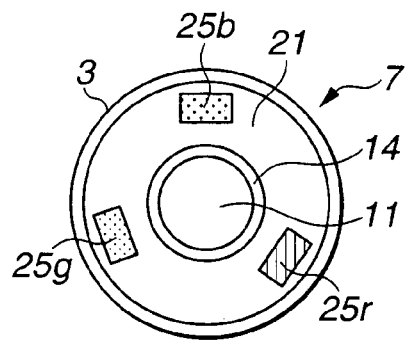

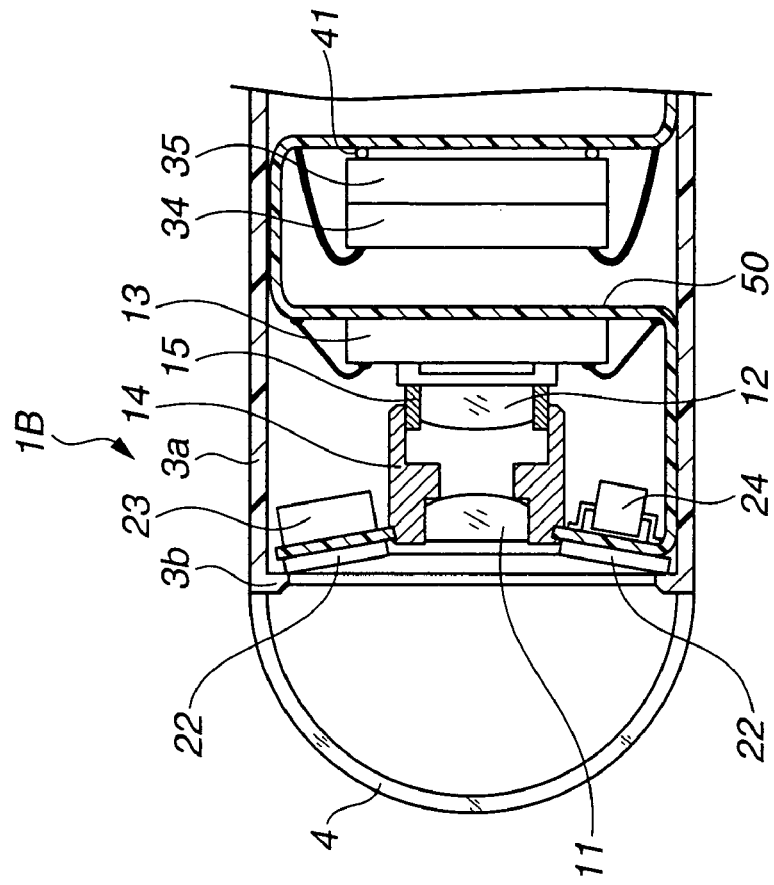
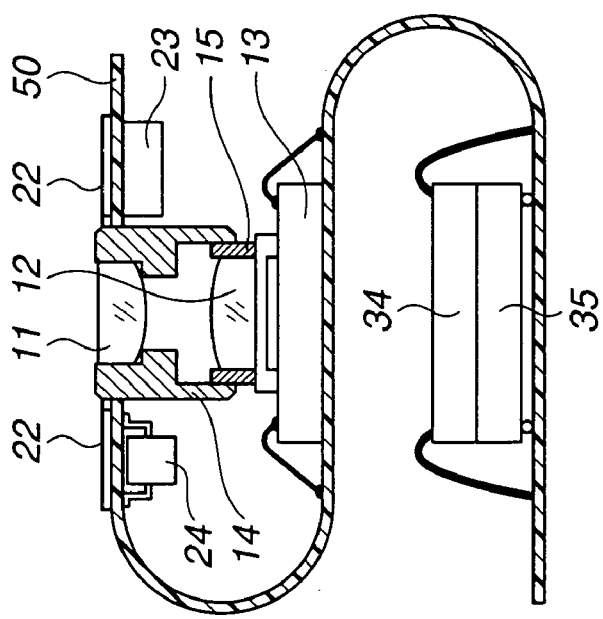
FIG. 5A
FIG. 5B

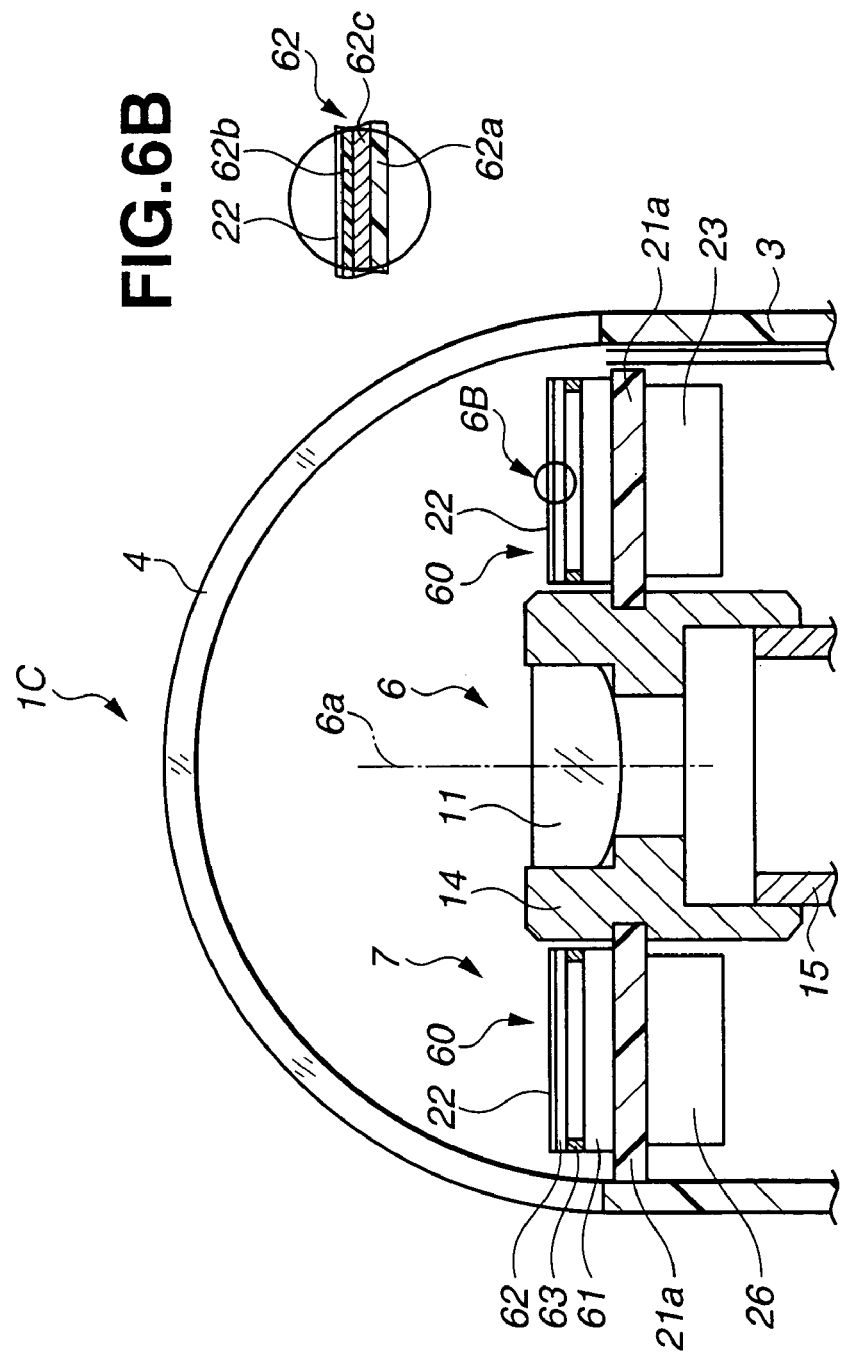

CAPSULE ENDOSCOPE WITH ELECTROLUMINESCENCE LIGHT SOURCE

This application claims benefit of Japanese Application No. 2003-72665 filed on Mar. 17, 2003, the contents of which are incorporated by this reference.

BACKGROUND OF THE INVENTION

1. Field of the Invention

The present invention relates to a capsule endoscope which picks up an image of the body cavity by introducing, in the living body, a capsule portion incorporating an observation optical unit and an illuminating unit.

2. Description of the Related Art

Recently, an endoscope apparatus has recently been used. In the endoscope apparatus, an observing unit arranged to an edge portion of an elongated inserting portion of an endoscope is inserted to an observed portion in the body cavity as a target. The observing unit faces the observed portion as the target and thus an observed image of the observed portion as the target is displayed on a screen of an observing device.

The endoscope in the endoscope apparatus comprises an observing unit which captures an image of a subject in the body cavity and an observing device which displays an observed image, which are connected by an elongated inserting portion. Therefore, the inserting portion needs to be inserted near the observed portion as the target so that the observing unit faces the observed portion as the target and the observed image is obtained. However, the inserting portion must be smoothly introduced near the observed portion as the target with skilled art.

In recent years, a capsule endoscope apparatus integrally having a capsule endoscope and an observing device has been proposed. The capsule endoscope integrally includes an observation optical unit, an illuminating unit, and a receiving and transmitting device in a capsule portion.

Therefore, the capsule portion is swallowed like a tablet and then the observed image of the subject captured by the observing unit is transmitted to the observing device as an external device via the receiving and transmitting device. Thus, the observed image of the subject captured by the observing unit in the capsule portion is displayed on a screen of the observing device.

For example, Japanese Unexamined Patent Application Publication No. 2001-91860 discloses a capsule endoscope. The capsule endoscope includes an objective lens in an inner space formed by approximately semi-spherical transparent cover and a light emitting diode arranged to sandwich the objective lens. In the capsule endoscope, a subject is illuminated by the light emitting diode, an image of the subject is formed on an image sensor by an objective optical system, and the observed image is obtained.

SUMMARY OF THE INVENTION

According to the present invention, a capsule endoscope includes a capsule portion. The capsule portion includes at least an observation optical unit having an image pick-up element and an optical lens that forms an objective optical system, an illuminating unit having an illuminating substrate, a surface emission light source, and a light-emitting control circuit, a peripheral-circuit part which forms various circuits having a signal processing circuit, a receiving and transmitting circuit, and a control circuit, and a power source unit which supplies power to the observation optical unit, the illuminating unit, and the peripheral-circuit part. Therefore, the luminance blur and light-distribution blur of illuminating light generated from the illuminating unit are solved. Further, the space of the capsule portion for providing the illuminating unit in the longitudinal direction can be reduced, thus, the capsule portion is reduced in size, and the space in the capsule portion is effectively used.

The above and other objects, features and advantages of the invention will become more clearly understood from the following description referring to the accompanying drawings.

BRIEF DESCRIPTION OF THE DRAWINGS

FIG. 2A is a diagram showing a state in which an EL device is formed on the entire surface around a lens frame;

FIG. 2B is a diagram showing a state in which the EL device is divided and is formed around the lens frame;

FIG. 2C is a diagram showing a state in which an EL device formed like matrixes of R, G, and B is formed on the entire surface around the lens frame;

FIG. 2D is an enlarged view of a portion shown by reference numeral 2D in FIG. 2C;

FIG. 2E is a diagram showing a state in which EL devices for red, green, and blue are formed as three divided ones;

FIG. 3A is a diagram showing an example of the arrangement of a surface emission laser;

FIG. 3B is a diagram showing a state in which surface emission lasers for red, green, and blue are arranged;

FIG. 5A is a diagram explaining a flexible substrate having an EL device;

FIG. 5B is a diagram explaining a state in which the flexible substrate is arranged in a capsule portion;

FIG. 6A is a diagram explaining a capsule endoscope having illuminating-direction changing means for changing an illuminating direction of an EL device;

FIG. 6B is an enlarged view of a portion shown by reference numeral 6B in FIG. 6A.

DESCRIPTION OF THE PREFERRED EMBODIMENTS

Hereinbelow, a description is given of embodiments of the present invention with reference to the drawings.

First Embodiment

Figure 1:
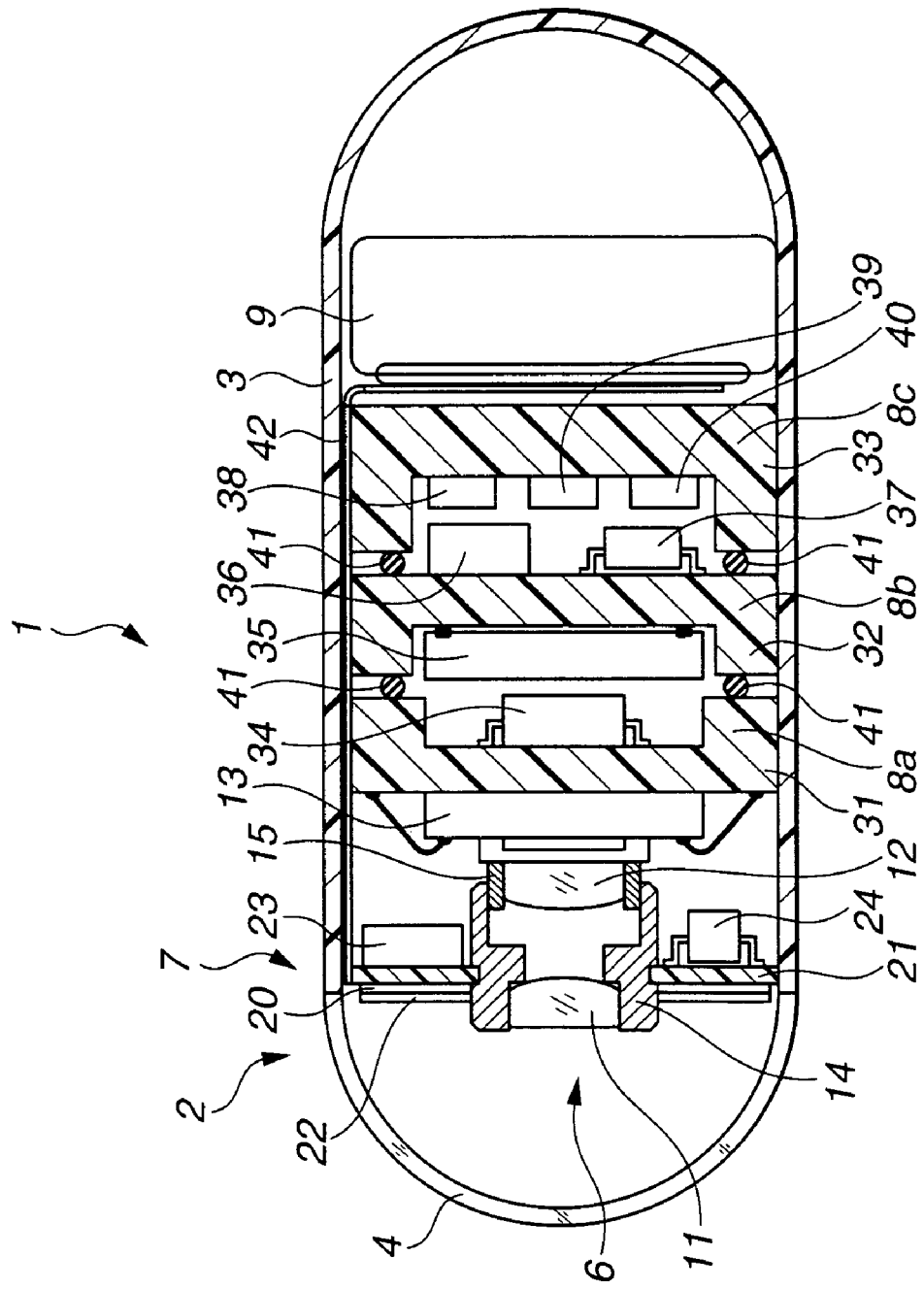
FIG. 1 is a diagram explaining the structure of a capsule endoscope.

Referring to FIG. 1, a capsule endoscope 1 comprises in a capsule portion 2: an observation optical unit; an illuminating unit; peripheral-circuit parts; and a power source unit according to the first embodiment, which will be described later.

The capsule portion 2 comprises: a capsule main body (hereinafter, simply abbreviated to a main body) 3; and an observing-side cover 4. The main body 3 is cylindrical by cylindrically shaping an end portion. The main body 3 is a hard resin member with the compatibility with the living body containing, for example, polysulfone.

The observing-side cover 4 is semi-spherical. The observing-side cover 4 is fixed and arranged in a watertight state on the edge side of the main body 3. The observing-side cover 4 is made of a transparent resin member. The resin member has predetermined optical transparency and compatibility with the living body.

The main body 3 comprises an observation optical unit 6, an illuminating unit 7, a plurality of peripheral-circuit parts 8a, 8b, and 8c and a power source unit 9 for supplying power. Further, the main body 3 includes a treatment tool and a tank for accumulating a drug solution (not shown).

The observation optical unit 6 mainly comprises: two optical lenses 11 and 12; an image pick-up element 13; a lens frame 14; and an image pick-up element frame 15. The optical lenses 11 and 12 have a circular cross-section and form an objective optical system. An optical image passes through the optical lenses 11 and 12 and is formed on an image pick-up surface of the image pick-up element 13. The lens frame 14 is a tube member with predetermined shape. The optical lenses 11 and 12 are fixed at predetermined positions of the lens frame 14. The image pick-up element frame 15 and the lens frame 14 are integrally fixed. The image pick-up element frame 15 is arranged to one-surface side of the image pick-up element 13. The first peripheral-circuit part 8a is fixed at a predetermined position on the other side of the image pick-up element 13.

The illuminating unit 7 comprises: an illuminating substrate 21; an electroluminescence device (hereinafter, referred to as an EL device) 22; and various electronic parts 23 and 24 forming a light-emitting control circuit.

The illuminating substrate 21 is shaped like an extended play record. Therefore, the lens frame 14 is arranged to the inner-periphery side of the illuminating substrate 21. The illuminating substrate 21 is made of an organic member or inorganic member. The EL device 22 is a surface emission light source which is made of a thin film or a thick film. This film is made of a low-molecular-weight organic light-emitting material or a high-molecular-weight organic material, or inorganic light-emitting material, and is formed on one-surface side of the illuminating substrate 21. The electronic parts 23 and 24 are mounted on the other-surface side of the illuminating substrate 21. The electronic parts 23 and 24 form the light-emitting control circuit which controls a light-emitting state of the EL device 22.

The EL device 22 has the property that no heat is generated. In addition, as compared with a light-emitting diode used as a conventional illuminating unit, the EL device 22 has the property that the consumption power is considerably reduced.

The EL device 22 is formed on a transparent substrate 20 made of glass or polyethylene teleftarate (PET) by printing, deposition, sputtering, plating or the like. Specifically, referring to FIG. 2A, the EL device 22 which emits white light is formed on the entire surface of the transparent substrate 20 and is mounted on the illuminating substrate 21.

Referring to FIG. 2B, the EL device 22 is divided and formed on the surface of the transparent substrate 20 with a predetermined area, and is mounted on the illuminating substrate 21. The area of the EL element 22 is properly set and, thus, the brightness is adjusted and the subject can be illuminated with desired brightness.

The entire surface of the illuminating substrate 21 may be divided into a plurality of surfaces with a predetermined area to form the EL device 22 and the desired surface of the EL device 22 may properly emit light. Thus, the brightness of illuminating light can properly be changed in accordance with the observed position in the body cavity through which the capsule endoscope passes.

Further, the EL device 22 may directly be formed on the illuminating substrate 21. Alternatively, a condenser lens or diffusion lens may be arranged on the EL device 22.

Referring to FIGS. 2C and 2D, the EL device 22a having the R, G, B matrixes is formed on the entire surface of the illuminating substrate 21. Or, referring to FIG. 2E, a red EL device 22r, a green EL device 22g, and a blue EL device 22b are formed as three divided portions on the surface of the illuminating substrate 21 and are colored to white by complementary colors. Then, white light-emission is efficiently possible. Thus, a preferable observed image is obtained.

The peripheral-circuit parts 8a, 8b, and 8c comprise substrates 31, 32, and 33, and various electronic parts 34, . . . , 40. The substrates 31 to 33 have wirings with predetermined conductive patterns. The electronic parts 34 to 40 are mounted on the substrates 31 to 33. The peripheral-circuit parts 8a to 8c are electrically and mechanically connected by projecting electrodes 41. Thus, various circuits such as a signal processing circuit, a receiving and transmitting circuit, and a control circuit are arranged in the capsule portion 2.

The signal processing circuit performs processing for converting an optical image formed on the image pick-up surface of the image pick-up element 13 into an image signal and generates a driving signal for driving the image pick-up element 13. The receiving and transmitting circuit performs predetermined processing of the image signal generated by the signal processing circuit, transmits the image signal to the observing device as the external device (not shown), and receives the control signal transmitted from the observing device. The control circuit controls portions based on various control signals received by the receiving and transmitting circuit.

The power source unit 9 is, for example, a battery. The power source unit 9 and the illuminating unit 7 are electrically connected by a flexible substrate 42. Further, the power source unit 9 and the peripheral-circuit parts 8a to 8c are electrically connected by the flexible substrate 42.

The power source unit 9 is not limited to the battery and may be a power source unit or the like comprising a power-receiving magnetic coil for receiving magnetic force outputted from the external device (not shown) and a charge capacitor.

A description is given of the operation of the capsule endoscope 1 with the above-mentioned structure.

First, an examinee swallows the capsule endoscope 1. Thus, the capsule endoscope 1 is introduced in the body cavity via the mouth cavity.

Next, an operator operates the observing device and transmits an observation instructing signal for endoscope observation and the like to the capsule endoscope 1. Then, the receiving and transmitting circuit in the capsule endoscope 1 receives the observation instructing signal and thus the EL device 22 in the illuminating unit 7 enters the light emitting state and the image pick-up element 13 in the observation optical unit 6 enters the image pick-up state.

The illuminating light without luminance blur obtained by surface-emitting light by the EL device 22 uniformly illuminates the subject. When the image pick-up element 13 is in the image pick-up state, the optical image of the subject illuminated by the EL device 22 is formed on the image pick-up surface of the image pick-up element 13 via the observing-side cover 4 and the optical lenses 11 and 12. The optical image formed on the image pick-up surface is converted into an electric signal by the image pick-up element 13. The converted electric signal is converted into an image signal by the signal processing circuit. Then, the converted image signal is transmitted to the observing device via the receiving and transmitting circuit. The image signal transmitted to the observing device is outputted to a display device (not shown) in the observing device. Consequently, an endoscope image captured by the capsule endoscope 1 is displayed on a screen of the display device.

As described above, the illuminating unit in the capsule endoscope is the surface emission light source comprising the EL device containing a film on the surface of the substrate. Therefore, the thickness dimension of the capsule portion in the optical unit can considerably be thinner in the longitudinal direction.

The EL device formed as the surface on the substrate as the illuminating unit in the capsule endoscope surface-emits light. Thus, the uniform illuminating light can be obtained with excellent light-distribution and without luminance blur.

Further, the EL device forming the illuminating unit in the capsule endoscope has the property that no heat is generated. Thus, it is possible to accurately prevent the inconvenience that the heat generated by the illuminating unit is transmitted to the image pick-up element, the temperature of the image pick-up element increases, and noises generate. Further, the power consumption of the illuminating unit is considerably reduced.

With the above structure and operations, a preferable endoscope image is obtained by the capsule endoscope. Moreover, it is possible to effectively use the space in the capsule portion forming the capsule endoscope, to reduce the size of the capsule portion, and to effectively use power.

According to the first embodiment, the surface emission light source comprises the EL device containing the film. Further, the surface emission light source may comprise a surface emission laser. As compared with the surface emission laser, the surface emission laser in this case can be thinner. Furthermore, since the contact area to a holding member is large, the surface emission laser has the property that a cooling effect is high and a stable output is obtained.

In the case of using the surface emission laser as the surface emission light source, referring to FIG. 3A, a plurality of surface emission lasers 25 which emits white light at a predetermined position on the illuminating substrate 21 are arranged at predetermined positions. Alternatively, referring to FIG. 3B, a surface emission red laser 25r, a surface emission blue laser 25b, and a surface emission green laser 25g are arranged at predetermined positions on the illuminating substrate 21. Thus, the white light may be combined. A condenser lens or a diffusion lens may be arranged onto the upper surface of the surface emission laser.

As a result, the surface emission laser has preferable light directivity and therefore the illuminating light is illuminated to a target position with stable brightness.

Second Embodiment

The illuminating substrate 21 is arranged at the position approximately perpendicular to the capsule portion 2 in the longitudinal direction according to the first embodiment. However, the surface emission light source forming the illuminating unit 7 arranged to the capsule endoscope 1 may be arranged with the following structure.

Figure 4:
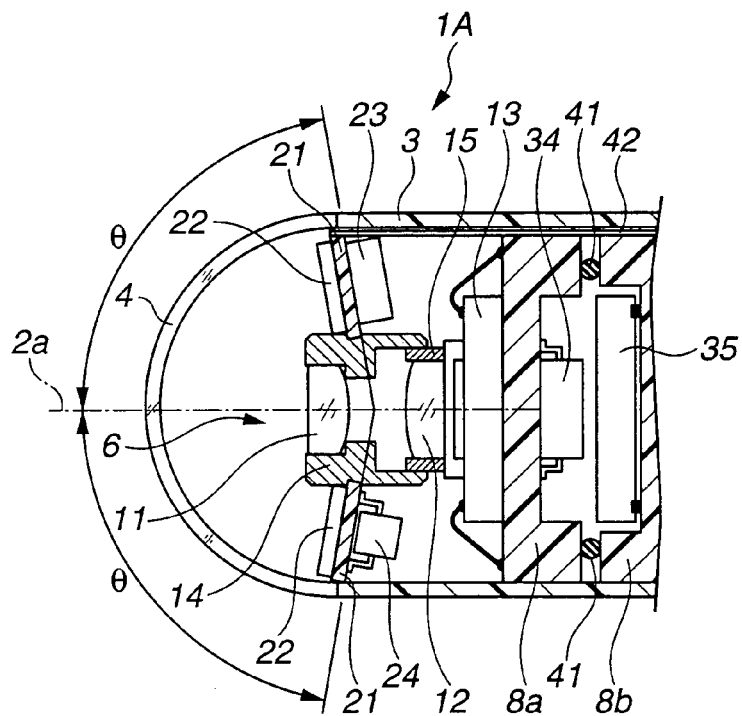
FIG. 4 is a diagram explaining a capsule endoscope in a state in which an observation optical unit is arranged to an illuminating substrate as a feature.

That is, referring to FIG. 4, the illuminating substrate 21 having the EL device 22 and the electronic parts 23 and 24 is arranged with the inclination having a predetermined angle $\theta$ to the capsule portion in the longitudinal direction thereof.

Thus, the illuminating direction of the illuminating light emitted from the EL device 22 formed on the illuminating substrate 21 is properly set to a desired direction.

Other structures are the same as those according to the first embodiment, the same members are designated by the same reference numerals, and a description thereof is omitted.

As stated above, the illuminating substrate forming the illuminating unit in the capsule endoscope is arranged with the inclination of the predetermined angle $\theta$ to the capsule portion in the longitudinal direction thereof. Consequently the illuminating direction of the illuminating light is properly set matching the observing target, the illuminating efficiency is improved, and the brightness of the observing portion is set.

Referring to FIG. 5A, according to the second embodiment, a flexible substrate 50 having the flexibility is used in place of the illuminating substrate 21 having the EL device 22 and the electronic parts 23 and 24 and the substrates 31 to 33 having the various electronic parts 34 to 40. Wiring patterns are formed on both the front and back surfaces of the flexible substrate 50 with predetermined shape.

The EL device 22 is directly formed at the predetermined position of the flexible substrate 50. The electronic parts 23 and 24, the image pick-up element 13, and the electronic parts 34 to 40 are mounted on predetermined positions by a flip chip, wire bonding or the like in consideration that they are bent and arranged in the main body 3.

Referring to FIG. 5B, a capsule endoscope 1B is formed such that the flexible substrate 50 is bent like a ring in the inner space of a main body 3a. A substrate supporting portion 3b projected with a predetermined amount in the circumferential direction is formed at a predetermined position of the inner-peripheral surface of the main body 3a. The substrate supporting portion 3b is used for setting the edge portion of the flexible substrate 50 at a predetermined position.

Therefore, by arranging the edge portion of the flexible substrate 50 at the substrate supporting portion 3b, the observation using the endoscope is performed by setting, in a desired direction, the illuminating direction of the illuminating light emitted from the EL device 22 formed on the flexible substrate 50.

Other structures are the same as those according to the first embodiment, the same member is designated by the same reference numeral, and a description thereof is omitted.

Prior to the electronic part 34, the electronic part 35 is electrically and mechanically connected to the flexible substrate 50 via a projecting electrode 41 by using the ultrasonic waves, thermocompression, soldering or the like. While the electronic part 34 is arranged on the electronic part 35, the electronic part 34 is electronically and mechanically connected to the flexible substrate 50 by using the ultrasonic waves, thermocompression, soldering, ACP, NCP or the like. After connection, the connecting peripheral portion is fixed by a fixing agent of an epoxy system, a phenol system, a silicon system, an acrylic system or the like.

As mentioned above, the EL device is formed on the flexible substrate and the electronic parts are mounted on the flexible substrate. Thus, the number of assembling processes and the number of parts are reduced.

By properly setting the position of the substrate supporting portion formed on the main body, the illuminating direction emitted from the EL device is set to the desired direction.

Other operation and advantages are the same as those according to the first embodiment.

Referring to FIG. 6A, in a capsule endoscope 1C according to the second embodiment, the EL device 22 is formed on a variable focusing member 60 as illuminating direction changing means. The variable focusing member 60 is arranged on an illuminating substrate 21*a*.

The variable focusing member 60 mainly comprises a bottom electrode 61, a top electrode 62, and a spacer member 63. The bottom electrode 61 is arranged onto the illuminating substrate 21*a*. The top electrode 62 faces the bottom electrode 61 and is arranged thereto via the spacer member 63. The spacer member 63 has a predetermined electrostatic gap between the bottom electrode 61 and the top electrode 63.

Specifically, referring to FIG. 6B, the top electrode 62 comprises: a first insulating resin film 62*a* and a second insulating resin film 62*b* which are made of a polyimide resin member or the like; and an electrode 62*c* made of an aluminum sandwiched by the first and second insulating resin films 62*a* and 62*b*. The EL device 22 is formed on the second insulating resin film 62*b*.

Reference numeral 26 denotes an electronic part forming a focusing position control circuit which controls the focusing position of the variable focusing member 60.

A description is given of the operation for the EL device 22 which is arranged to the variable focusing member 60 with the above-described structure.

An observation instructing signal is transmitted to the capsule endoscope 1C, and a receiving and transmitting circuit in the capsule endoscope 1C receives the observation instructing signal. Thus, the EL device 22 of the illuminating unit 7 emits light and the image pick-up element 13 of the observation optical unit 6 enters the image pick-up state. Then, the EL device 22 outputs the illuminating light substantially in parallel with an optical axis 6*a* of the observation optical unit 6.

Here, an observing device (not shown) transmits a focusing change instructing signal to the capsule endoscope 1C. Then, the focusing position control circuit applies a predetermined voltage to the bottom electrode 61 and the top electrode 62. Then, an electric field is generated between the electrodes, and the top electrode 62 is concave-bent. This change inclines the illuminating light outputted from the EL device 22 to the optical axis 6*a* of the observation optical unit 6. That is, the top electrode 62 is modified in a predetermined state, thereby changing the output direction of the illuminating light outputted from the EL device 22.

As mentioned above, the surface emission light source is formed at the predetermined position of the variable focusing member. Thereby, the focusing instructing signal is outputted during the observation, the shape of the variable focusing member is modified, and the output direction of the illuminating light outputted from the surface emission light source can be changed to the desired direction.

Thus, the proper illuminating light illuminates the observed position and the preferable endoscope image is obtained.

Other operation and advantages are the same as those according to the first embodiment.

Figure 7:
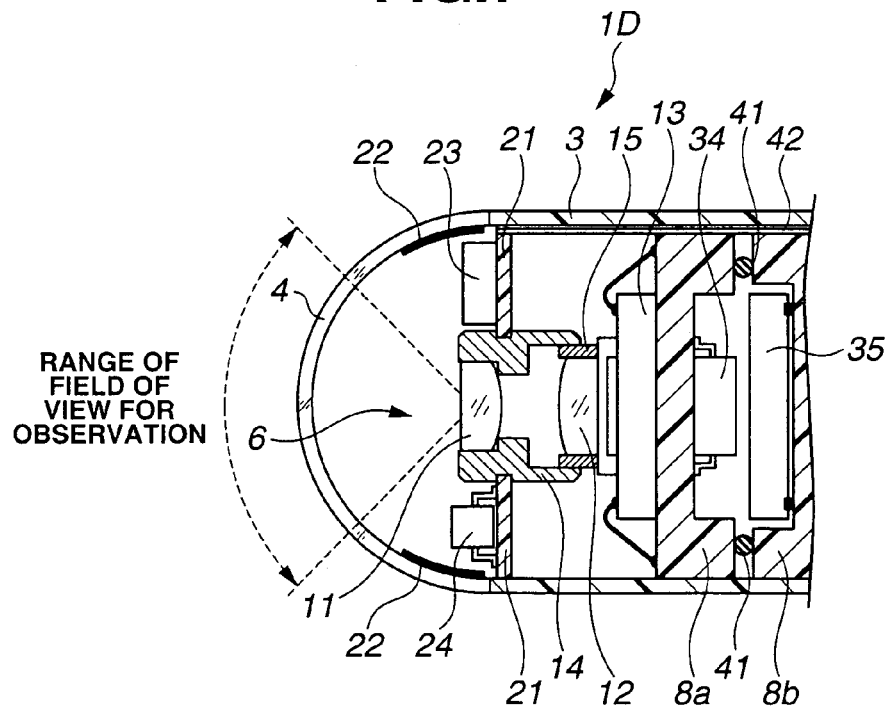
FIG. 7 is a diagram explaining a capsule endoscope having the arrangement position for the EL device as a feature.

Referring to FIG. 7, in a capsule endoscope 1D according to the second embodiment, the EL device 22 is formed like a band or partly at a predetermined position out of the observing field-of-view range shown by a broken line of the observation optical unit 6 on the inner peripheral surface of the observing-side cover 4, instead of forming the EL device 22 on the illuminating substrate 21. The electronic parts 23 and 24 forming the control circuit which controls the light emitting state of the EL device 22 are arranged on the edge surface side of the illuminating substrate 21.

Other structures are the same as those according to the first embodiment, the same member is designated by the same reference numeral, and a description thereof is omitted.

As mentioned above, the surface emission light source formed by the film is formed at the predetermined position on the inner surface of the observing-side cover, and the light-emitting control circuit parts are arranged on the illuminating substrate on the inner-surface side of the observing cover. Thus, the space in the capsule portion forming the capsule endoscope is effectively used or the capsule portion is reduced in size.

Other operation and advantages are the same as those according to the first embodiment.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A capsule endoscope comprising a capsule portion, the capsule portion comprising at least:
   an observation optical unit having an image pick-up element and an optical lens that forms an objective optical system;
   an illuminating unit having an illuminating substrate, an electroluminescence device as a light source, and a light-emitting control circuit;
   peripheral-circuit parts which form various circuits including a signal processing circuit, a receiving and transmitting circuit, and a control circuit; and
   a power source unit which supplies power to the observation optical unit, the illuminating unit, and the peripheral-circuit parts,
   wherein the electroluminescence device is arranged around the observation optical unit, so that the electroluminescence device is formed on one of the entire surface of a transparent substrate mounted on the illuminating substrate and directly on the entire surface of the illuminating substrate.

2. A capsule endoscope according to claim 1, wherein the electroluminescence device is formed as an R-, G-, and B- matrix.

3. A capsule endoscope according to claim 1, wherein the electroluminescence device is divided and is arranged on the illuminating substrate.

4. A capsule endoscope according to claim 3, wherein the electroluminescence device is divided into sources for R, G, and B and is arranged.

5. A capsule endoscope according to claim 1, wherein the electroluminescence device has an optical member for light condensing or diffusion on a top surface thereof.

6. A capsule endoscope according to claim 1, wherein the electroluminescence device is formed on a variable focusing member as illuminating direction changing means arranged on the illuminating substrate.

7. A capsule endoscope according to claim 6, wherein the illuminating direction changing means comprises:

a bottom electrode arranged on the illuminating substrate;
a top electrode arranged facing the bottom electrode; and
a spacer member which forms a predetermined electrostatic gap between the bottom electrode and the top electrode.

8. A capsule endoscope comprising a capsule portion, the capsule portion comprising at least:
- an observation optical unit having an image pick-up element and an optical lens that forms an objective optical system;
- an illuminating unit having an illuminating substrate, an electroluminescence device as a light source, and a light-emitting control circuit;
- peripheral-circuit parts which form various circuits including a signal processing circuit, a receiving and transmitting circuit, and a control circuit; and
- a power source unit which supplies power to the observation optical unit, the illuminating unit, and the peripheral-circuit parts, wherein the electroluminescence device is arranged on an inner peripheral surface of an observing-side cover out of the observing field of view range of the observation optical unit.

* * * * *